United States Patent [19]
Chin et al.

[11] Patent Number: 5,370,134
[45] Date of Patent: Dec. 6, 1994

[54] METHOD AND APPARATUS FOR BODY STRUCTURE MANIPULATION AND DISSECTION

[75] Inventors: Albert K. Chin, Palo Alto; Frederic H. Moll, San Francisco, both of Calif.

[73] Assignee: Orgin Medsystems, Inc., Menlo Park, Calif.

[21] Appl. No.: 762,318

[22] Filed: Sep. 19, 1991

Related U.S. Application Data

[63] Continuation-in-part of Ser. No. 706,781, May 29, 1991, abandoned.

[51] Int. Cl.⁵ .................. A61B 19/00; A61M 29/00
[52] U.S. Cl. .................. 128/898; 606/191; 606/167; 604/104
[58] Field of Search .................. 604/96–102, 604/104, 164, 170; 606/49, 108, 127, 167, 169, 171, 172, 180, 185, 190, 191, 192, 198; 128/898

[56] References Cited

U.S. PATENT DOCUMENTS

| | | | |
|---|---|---|---|
| 3,168,092 | 2/1965 | Silverman | 128/1.2 |
| 4,137,906 | 2/1979 | Akiyama et al. | 128/2 A |
| 4,271,839 | 6/1981 | Fogarty et al. | 128/344 |
| 4,318,410 | 3/1982 | Chin | 128/325 |
| 4,430,076 | 2/1984 | Harris . | |
| 4,493,711 | 1/1985 | Chin et al. | 604/271 |
| 4,863,440 | 9/1989 | Chin | 604/271 |
| 4,966,583 | 10/1990 | Debbas | 604/98 |
| 5,159,925 | 11/1992 | Neuwirth et al. | 128/401 |
| 5,183,463 | 2/1993 | Debbas | 604/96 |
| 5,183,464 | 2/1993 | Dubrul et al. | 604/96 |
| 5,195,959 | 3/1993 | Smith | 606/41 |
| 5,197,948 | 3/1993 | Ghodsian | 604/96 |
| 5,197,971 | 3/1993 | Bonutti | 604/96 |
| 5,201,752 | 4/1993 | Brown et al. | 606/190 |

OTHER PUBLICATIONS

Pietrafitta et al. (1991) Gastrointestinal Endoscopy 37:338–343.

*Primary Examiner*—Ren Yan
*Attorney, Agent, or Firm*—Townsend and Townsend Khourie and Crew

[57] ABSTRACT

Hollow body structures may be manipulated and dissected from surrounding tissue using a manipulator device and a dissection device. The manipulator includes a rigid shaft having an inflatable balloon at its distal end. By inserting the balloon through a wall of the body structure and inflating the balloon, the body structure can be manipulated using the shaft to expose a dissection plane in an optimum manner. The dissection device is used to separate the body structure from its surrounding tissue. The separator device includes a separator head which is a cylindrical body having a plurality of axial channels therein. The dissector head is rotated or oscillated at a high frequency and acts to separate the body structure from the surrounding tissue with minimum damage.

31 Claims, 4 Drawing Sheets

METHOD AND APPARATUS FOR BODY STRUCTURE MANIPULATION AND DISSECTION

This application is a continuation-in-part of application Ser. No. 07/706,781, filed on May 29, 1991, now abandoned, the full disclosure of which is incorporated herein by reference.

BACKGROUND OF THE INVENTION

1. Field of the Invention

The present invention relates generally to the structure and use of surgical instruments, and more particularly to a method and apparatus for manipulating and dissecting body structures during surgical procedures.

Minimally invasive surgical (MIS) techniques, such as laparoscopic, endoscopic, and arthroscopic surgery, are generally performed through small incisions using specialized instruments to accomplish the desired surgical procedure. Usually, the instruments are introduced through a narrow-diameter tube, such as a trocar sleeve, while the physician observes manipulation of the instruments through specialized imaging equipment, such as laparoscopes, endoscopes, and arthroscopes. Such MIS techniques offer significant advantages over conventional "open" surgical procedures. In particular, the MIS techniques are usually less traumatic, require a shorter recovery time, and are less costly than corresponding conventional surgical procedures.

Of particular interest to the present invention are laparoscopic cholecystectomy procedures where the gallbladder is surgically severed (commonly referred to as dissected) and withdrawn through a small trocar sleeve, typically having a diameter of about 10 mm. In order to manipulate the gallbladder, several grasping forceps are introduced through additional trocar sheaths, and the position of the gallbladder is constantly changed in order to expose the interface between the gallbladder and surrounding tissue, particularly the liver, to permit dissection. The actual dissection has usually been performed using forceps, hooks, and/or a small gauze pledget to tear and tease the gallbladder from the surrounding tissue along the dissection plane.

While laparoscopic cholecystectomy procedures have been very successful and have become increasingly common, the need to simultaneously handle multiple graspers as well as a dissection instrument places great demands on the physician and usually requires coordination with one or more surgical assistants. The difficulty in performing the procedure is exacerbated by the slickness of the gallbladder surface, and overly vigorous attempts to capture the gallbladder can result in perforation, bile spillage, and gallbladder collapse. A collapsed gallbladder is even more difficult to dissect from the surrounding tissue than an intact gallbladder.

For these reasons, it would be desirable to provide improved methods and apparatus for manipulating and dissecting gallbladders during laparoscopic cholecystectomy procedures. It would be particularly desirable if such methods and apparatus were suitable for performing manipulation and dissection of other body structures during other surgical procedures. The method and apparatus should provide for controlled movement and manipulation of the body structure, preferably using a single instrument that can be manipulated by the physician with one hand. In the case of the gallbladder, the instrument should minimize the likelihood of bile spillage and should assure that the gallbladder remains expanded, preferably distended, to better present the dissection plane during the procedure. The method and apparatus should further provide for improved dissection techniques with reduced bleeding and tearing of the gallbladder, optionally providing for electrocautery capabilities.

2. Description of the Background Art

U.S. Pat. No. 4,430,076, describes a device for manipulating the uterus during examination procedures. The device is a handle having a balloon at its end, where the balloon is introduced through the cervix, inflated, and the handle is used to manipulate the uterus for examination purposes. Pietrafitta et al. (1991) Gastrointestinal Endoscopy 37:338-343, discloses the use of a dilating balloon to distend the pylorus during laparoscopic pyloromyotomy.

SUMMARY OF THE INVENTION

According to the present invention, improved methods and apparatus are provided for manipulating and dissecting body structures during surgical procedures, such as the gallbladder during laparoscopic cholecystectomy procedures. The methods comprise introducing an expandable member disposed on the distal end of a rigid shaft into the interior of the body structure, usually through a penetration in the body structure wall. The expandable member is then expanded to occupy at least a major portion of the interior volume, and the body structure can then be manipulated using the proximal end of the rigid shaft which remains available to the treating physician outside of the patient's body. Using the shaft, the physician can manipulate the hollow body structure with a single hand and can dissect the structure from surrounding tissue using a dissection instrument with the other hand. Positioning of the body structure is much easier and can be more precisely controlled than was possible using multiple grasping instruments. Moreover, the need to employ surgical assistants for positioning the body structure is reduced or eliminated entirely. Additionally, internal expansion of the body organ permits distention (over expansion) to better present the dissection plane during the dissection procedure.

In a first preferred aspect of the present invention, the expandable member and shaft are introduced through a penetration formed by advancing a sharp tip at the distal end of the shaft through a wall of the body structure. The expandable member is disposed proximally of the sharp tip and enters the interior of the body structure by continuing to advance the shaft in the direction of penetration. Usually, the sharp tip will be protected immediately after the initial penetration in order to prevent undesired perforations or other injury to the body structure. Protection can be achieved by either retraction or shielding of the tip, as described in more detail in connection with the apparatus hereinafter. In some cases, however, the dissection method of the present invention will rely on introducing the shaft and expandable member through a natural body orifice and will not require penetration of a wall of the body structure.

In a second preferred aspect of the method of the present invention, the gallbladder will be drained of bile prior to expansion of the expandable member, and the wall penetration will be aspirated during the remainder of the procedure to prevent bile leakage. Such drainage and aspiration are preferably effected by using particular drainage and aspiration lumens within the apparatus of the present invention, as described in more detail hereinbelow.

Apparatus according to the present invention include a device for manipulating the hollow body structure, where the device comprises a rigid shaft having a proximal end and a distal end, and an expandable member disposed near the distal end of the shaft. The expandable member is usually an elastic balloon which can expand and conform to the interior of the hollow body structure, although other expansion means such as expandable cages and coils would also be suitable.

A first embodiment of the manipulating device will include both a sharp tip and a blunt tip disposed near the distal end of the rigid shaft. Means will be provided for axially translating the sharp tip relative to the blunt tip, so that the sharp tip can be advanced and exposed during the initial stages of the procedure when the wall of the body structure is to be penetrated. After the device has entered the interior of the body structure, the blunt tip can then be advanced relative to the sharp tip (or the sharp tip retracted relative to the blunt tip) to protect the sharp tip and reduce the risk of unintended perforations and other injuries to the body structure.

In a second embodiment, the manipulation device of the present invention will include means for draining bile from the interior of the gallbladder and for aspirating leakage which may occur around the site of device penetration into the gallbladder. The drainage means will usually comprise a lumen within the rigid shaft which can be connected at its proximal end to a suitable vacuum (aspiration) source. The aspiration means will usually comprise an outer tube or sleeve which is coaxially disposed over the rigid shaft. The aspiration sleeve will usually include a resilient tip which can seal about the site of penetration, and the proximal end of the sleeve will be attached to a suitable vacuum (aspiration) source. Numerous specific designs for providing the desired drainage and aspiration capabilities may be provided.

Apparatus according to the present invention also include a dissection device comprising a shaft having a specialized dissection head. The dissection head comprises a cylindrical body having a plurality of axially oriented channels circumferentially spaced-apart thereabout. Means are provided for driving the dissection head, either by rotation or oscillation, at a relatively high rate, typically in the range from about 2000 rpm or Hz to 20,000 rpm or Hz. Preferably, the dissection head will have a length in the range from 2 mm to 20 mm, preferably from about 5 mm to 15 mm, a diameter in the range from 1 mm to 10 mm, preferably from about 1.5 mm to about 4 mm, and from about 4 to 10 axial channels disposed thereabout. Such a dissection device has been found to effectively separate body structures, such as the gallbladder from surrounding tissues, with a minimum of tearing and bleeding in either the body structure or the tissue.

Methods according to the present invention will further comprise use of the dissection device, either in combination with the manipulator device or separately from the manipulation device.

DESCRIPTION OF THE SPECIFIC EMBODIMENTS

Figure 1:
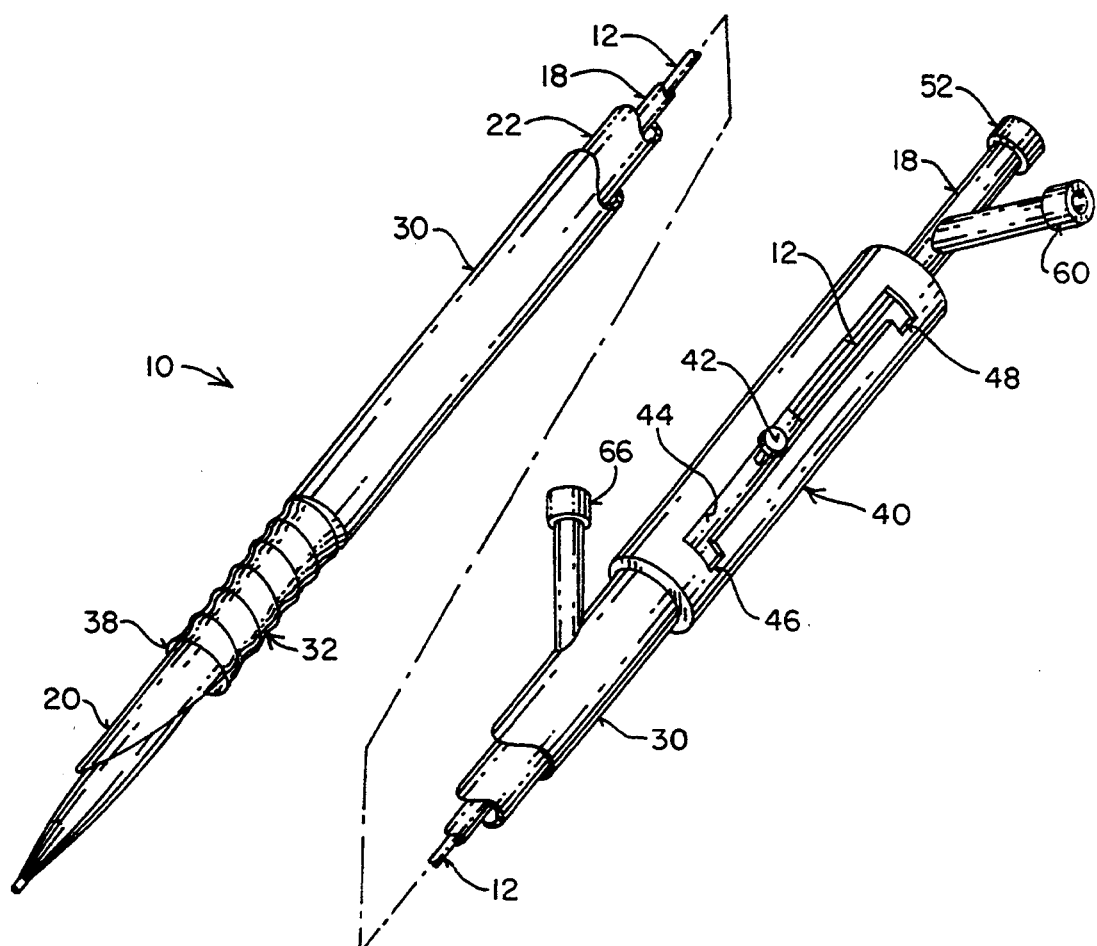
FIG. 1 is a perspective view of a body structure manipulator device constructed in accordance with the principles of the present invention.

The method and apparatus of the present invention are useful for manipulating and dissecting a variety of body structures in surgical procedures, particularly minimally invasive surgical (MIS) procedures where the apparatus are introduced through narrow diameter trocar sleeves and manipulated under the control of imaging equipment, as described generally above. While the methods and apparatus are particularly useful for removing the gallbladder during laparoscopic cholecystectomy procedures, as will be described in detail below, and they will also be useful for treating other body organs and structures during other surgical procedures, both MIS and conventional open surgical procedures. For example, the methods and apparatus of the present invention will be useful for the partial or total removal of the stomach in gastrectomy procedures; manipulation of the intestines during bowel resection and other procedures; manipulation of the uterus in hysterectomy procedures; manipulation of a segment of the lung in lung resections; manipulation of pericardial cavity in cardiac diagnostic and therapeutic procedures including endocardial mapping, ablation, and defibrillation electrode placement; and the like. This list of body structures and procedures is not meant to be exhaustive, and the methods and apparatus of the present invention may find a variety of additional uses.

The methods of the present invention rely on introducing an expandable member to the interior volume of a hollow body structure, usually through a penetration formed in the wall of the structure. Direct entry of the expandable member through the structure wall is usually preferable to entry through a natural orifice, either because no natural orifice is available (e.g., in the case of the gallbladder) or because the entry path through the orifice is so long or tortuous that it impedes subsequent manipulation of the body structure (e.g., introduction through the esophagus into the stomach and through the vagina and cervix into the uterus). In some cases, however, it may be feasible to introduce the expandable member through a natural body orifice in such a way that permits subsequent manipulation, although it will generally be less preferred.

The expandable member will be located at the distal end of a rigid shaft which permits manipulation of the body structure from its proximal end. By "rigid" it is meant that the shaft will have minimum flexibility so that manipulation at the proximal end will be transmitted with minimum deflection to the distal end (where the expandable member is disposed within the body structure). Usually, the rigid shaft will be composed of metal, such as surgical stainless steel, although rigid plastic shafts may also find use.

In a preferred embodiment of the present invention, a sharp tip will be provided at or near the distal end of the rigid shaft. The sharp tip may be formed as a part of or integrally with the rigid shaft, or may be formed on a separate tubular or other member which is associated with the rigid shaft. The sharp tip is provided to effect the initial penetration through the body structure wall, and the method of the present invention will usually provide for protection or shielding of the sharp tip after the penetration has been made. Specific approaches for protecting the sharp tip will be described in more detail in connection with the apparatus hereinafter.

Once inside the hollow body structure, the expandable member will be expanded to fill at least a major portion of the interior volume. It will be appreciated that the degree of contact between the expandable member and the interior wall of the body structure will in large part determine the degree of control which can be exercised over the structure. Thus, by expanding the expandable member to occupy substantially the entire interior volume of the hollow body structure, a great degree of control can be obtained. In many cases, it will be desirable to expand the expandable member sufficiently to distend the body structure (i.e., stretch the structure outward in all directions) so that the structure is firmly held by the expandable member on the rigid shaft. Such distension allows highly controlled manipulation and also serves to expose the dissecting plane by stretching the boundary interface between the structure and the surrounding tissue. In this way, the body structure can be pushed, pulled, turned, and otherwise manipulated during the dissection or other procedure.

The methods of the present invention further provide for removal and containment of the contents of the body structure, minimizing the risk that the contents will be accidentally spilled or leaked during the procedure. In conventional cholecystectomy and other procedures, the contents of the body structure are normally not removed since they maintain the shape of the structure and facilitate dissection. With the present invention, however, it is possible to remove the contents and thereafter expand the body structure from the interior to maintain the desired shape and facilitate dissection. Conveniently, removal of the contents of the body structure can be achieved by drainage through the shaft while containment around the site of penetration is achieved using a separate sealing member.

Referring now to FIGS. 1-4, a first embodiment of a manipulation device 10 constructed in accordance with the principles of the present invention will be described. The manipulation device 10 comprises a rigid shaft 12 having an expandable member 14 located at its distal end. As illustrated, the expandable member 14 is an inflatable balloon formed from an elastic material, such as silicone rubber, latex rubber, or the like, which when inflated can conform to the interior surface of the hollow body structure. It will be appreciated, however, that a variety of other expandable members, such as expandable coils, expandable cages, and other conformable members could be provided in place of the balloon 14. Use of the balloon is particular convenient, and it is presently contemplated as the preferred mode for carrying out the invention.

The balloon 14 can be inflated through an annular inflation lumen 16 which is defined by an inflation tube 18 mounted coaxially about the rigid shaft 12. The inflation tube 18 may itself be rigid, e.g., a metal tube, or may be a flexible polymeric sheath formed over the shaft 12. Polymeric inflation sheaths may be rigid or flexible, although flexible sheaths will usually be non-elastic so that they will not expand substantially under the inflation pressure being applied to the inflatable balloon 14. A preferred material for the inflation tube 18 is surgical stainless steel since it enhances the rigidity of the shaft 12.

The manipulation device 10 will further include a sharp tip 20 disposed generally at the distal end of rigid shaft 12. In this particular embodiment, the sharp tip 20 is formed at the distal end of a rigid tube 22 which can be axially translated between a distally extended configuration (as illustrated in FIG. 2) where the sharp tip 20 defines the distal tip of device 10 and a retracted configuration (as illustrated in FIG. 3) where the inflation balloon 14 is exposed at the distal-most point of the device.

The manipulation device 10 further comprises a coaxial sleeve 30 formed over the tube 22 and terminating in a resilient tip element 32. The resilient tip element 32 is illustrated as a metal spring 34, typically composed of stainless steel, covered by a thin plastic or elastic membrane 36. The purpose of the resilient tip is to seal about the penetration formed by the sharp tip 20 in the wall of the body structure. The resilient tip 30 can conform to the exterior of the wall about the penetration and will compress against the force of spring 34 as the tip is urged against the wall of the body structure (after penetration). Other structures, such as bellows and accordion configurations, could also find use. The sleeve 30 itself will be generally rigid with sufficient hoop strength to withstand the negative pressure of aspiration. Various polymeric materials, such as polyethylene and polyvinyl chloride, will be suitable.

Figure 2:
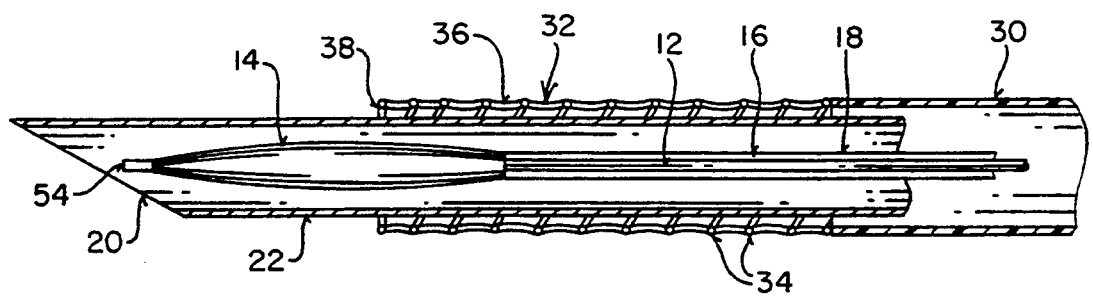
FIG. 2 is a side elevational view of the distal end of the device of FIG. 1, shown in section with a sharp tip element being advanced and a balloon element being deflated.
Figure 3:
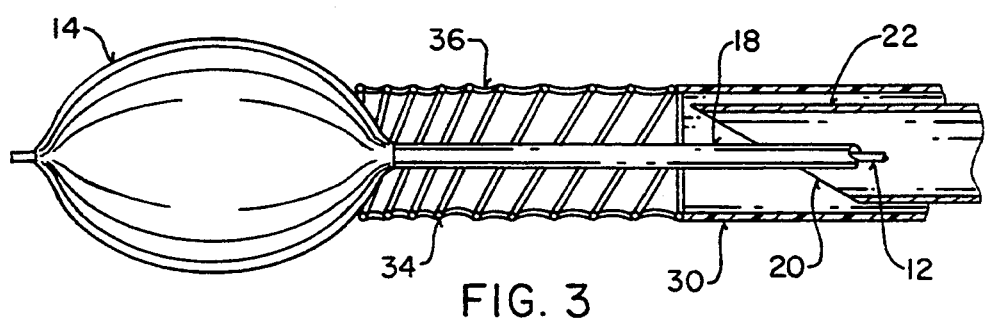
FIG. 3 is a side elevational view similar to FIG. 2, except that the sharp tip element has been retracted and the balloon element has been inflated.
Figure 4:
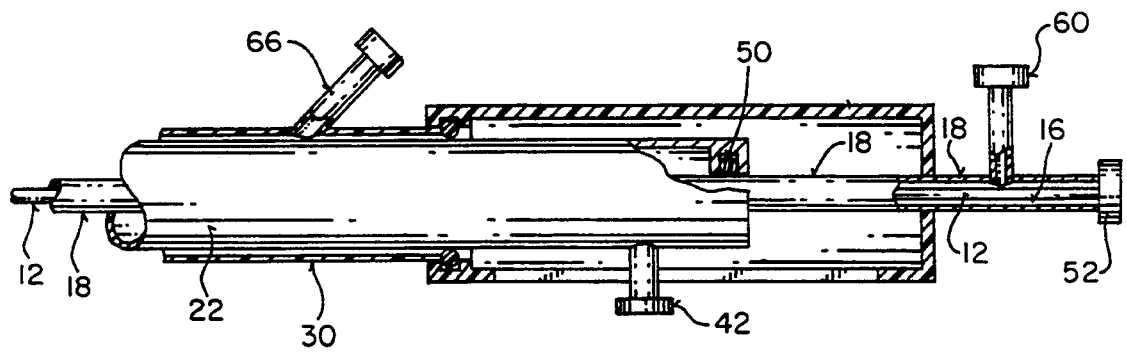
FIG. 4 illustrates the proximal end of the manipulator device of FIG. 1, shown in partial section with portions broken away.

In a preferred aspect of the present invention, the leading edge 38 of the resilient tip 32 will be located over the balloon 14, usually being located approximately half way down the length of the balloon as illustrated in FIG. 2. In this way, after the balloon is fully inserted into the desired body structure, the resilient tip will necessarily be compressed. The resulting spring force will assure that a relatively tight seal is achieved between the tip 32 and the outside wall of the body structure, further helping to minimize leakage.

A housing 40 is disposed at the proximal end of rigid shaft 12 and provides the necessary inflation and aspiration connections for the device, as well as providing means for axial translation of the sharp tip 20. Axial translation is effected by a handle 42 which is attached to the proximal end of the tube 22 which carries the sharp tip 20 at its distal end. The handle 42 travels in a slot 44 formed axially in the housing 40, including detents 46 and 48 for securing the tube 22 and tip 20 in their forwardmost and rearwardmost positions. An O-ring 50 provided at the proximal end of tube 22 to seal against the exterior of inflation tube 18. In this way, the open end of tube 22 is isolated from the outside (to inhibit gas leakage in laparoscopic procedures).

Rigid shaft 12 terminates at its proximal end in a connector 52 which may be interconnected with a suitable aspiration source (not illustrated) in order to drain the interior of the hollow body structure. The shaft 12 will typically be a hollow tube having an open distal end 54 so that the contents of the body structure can be drained by aspirating through the connector 52 after the shaft 12 has been introduced, typically prior to balloon inflation.

A second connector 60 is formed on the inflation tube 18 and communicates with the annular inflation lumen 16. In this way, balloon 14 can be inflated by applying an appropriate inflation medium, such as saline, air, or the like, through the connector 60. The inflation pressure will depend on the nature of the balloon 14 as well as the nature of the body structure being expanded. In the case of gallbladders being expanded with silicone rubber balloons, the inflation pressure will typically be in the range from about 0.5 to 5 psi, usually being in the range from about 1 to 2 psi. The total expanded volume of the balloon 14 (when used for gallbladder or manipulation) will typically be in the range from about 25 to 75 ml, usually being from 40 to 60 ml.

A third connector port 66 is provided on the coaxial sleeve 30 and is suitable for connection to an aspiration source. In this way, the region surrounding the penetration can be aspirated through the seal formed by resilient tip 32.

The overall dimensions of the device 10 will be selected depending on the hollow body structure being treated. For the treatment of the gallbladder, the device 10 will typically have a length in the range from about 30 to 75 cm, usually being from about 40 to 50 cm. The maximum diameter of the device, i.e., the outside diameter of the coaxial sleeve 30, will typically be less than 10 mm, preferably being in the range from about 5 mm to 7 mm.

Figure 5:
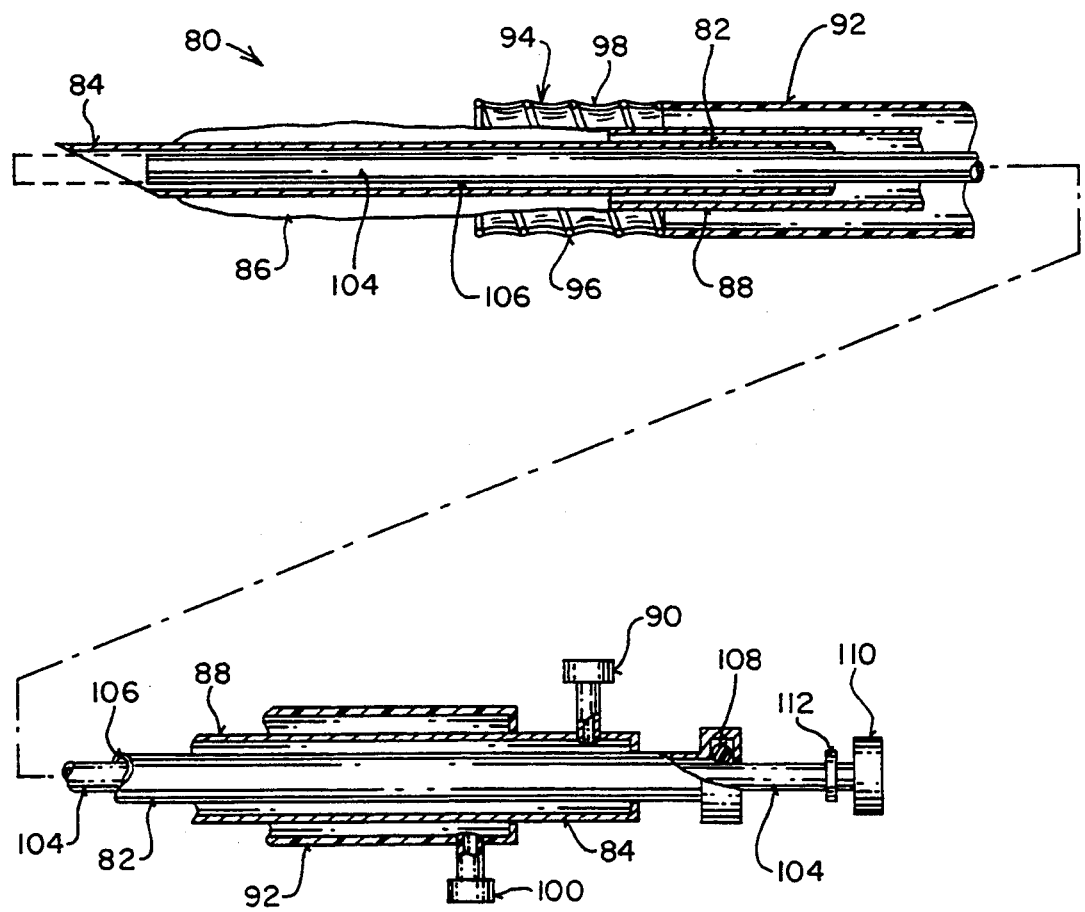
FIG. 5 illustrates an alternate embodiment of a manipulator device constructed in accordance with the principles of the present invention.

A second embodiment 80 of the manipulation device of the present invention is illustrated in FIG. 5. The device 80 comprises a rigid shaft 82 having a sharp tip 84 formed at its distal end. The rigid shaft 82 will usually be formed from metal or a rigid plastic, typically being surgical stainless steel. An inflatable balloon 86 is secured to the distal end of the rigid shaft 82 and will lie just proximally of the sharp tip 84. The balloon 86 will typically be composed of an elastic polymer, such as silicone rubber, and will be inflatable through an inflation tube 88 which is coaxially mounted over the rigid shaft 82. The inflation tube 88 is connected through a connector port 90 located at the proximal end thereof. An outer sleeve 92 is formed coaxially about the inflation tube 88 and terminates in a resilient tip 94, typically formed from a spring 96 and elastic membrane 98. The outer tube 92 is connected to an aspiration port 100 at its proximal end to permit aspiration around the penetration formed by sharp tip 84 when inserted through the wall of the body structure.

A protection rod 104 is slidably mounted in an axial lumen 106 of the rigid shaft 82. An O-ring 108 provides a sliding seal between the proximal end of rigid shaft and the exterior of protection rod 104 to isolate the interior of the body structure when the device 80 is in use. The protection rod 104 may be extended distally from rigid shaft 82, as illustrated in broken line, in order to protect the hollow body structure from the sharp tip 84 after the device has been inserted through the body structure wall. The protection rod 104 can be axially advanced and retracted simply by pulling on a proximal connector 110. A stop member 112 is provided to prevent over extension of the protection rod 104. Connector 110 also provides connection to a suitable aspiration source for drainage of the interior of the body structure. The protection rod 104 includes a hollow lumen which provides a drainage path through the device 80.

Figure 6:
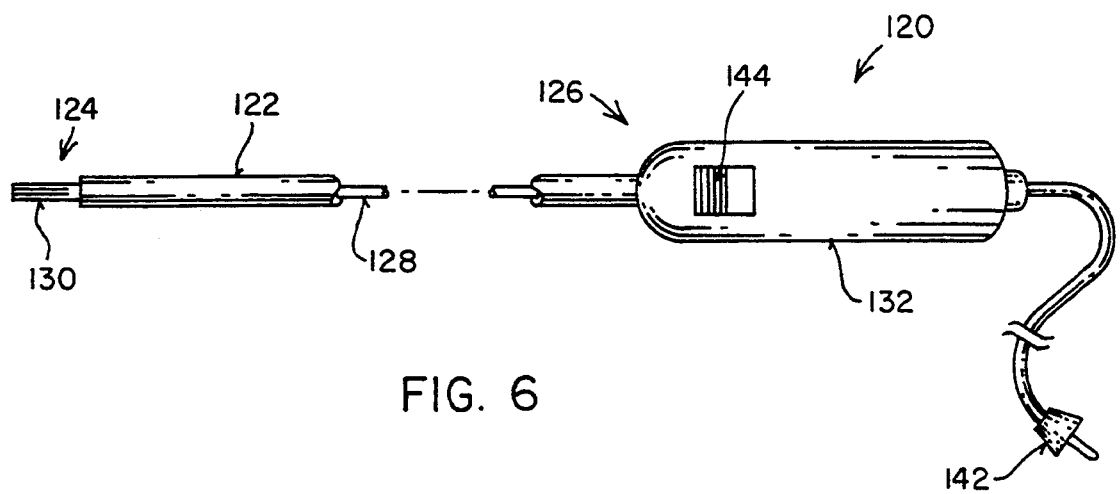
FIG. 6 is a side elevational view of a dissection device constructed in accordance with the principles of the present invention.
Figure 7:
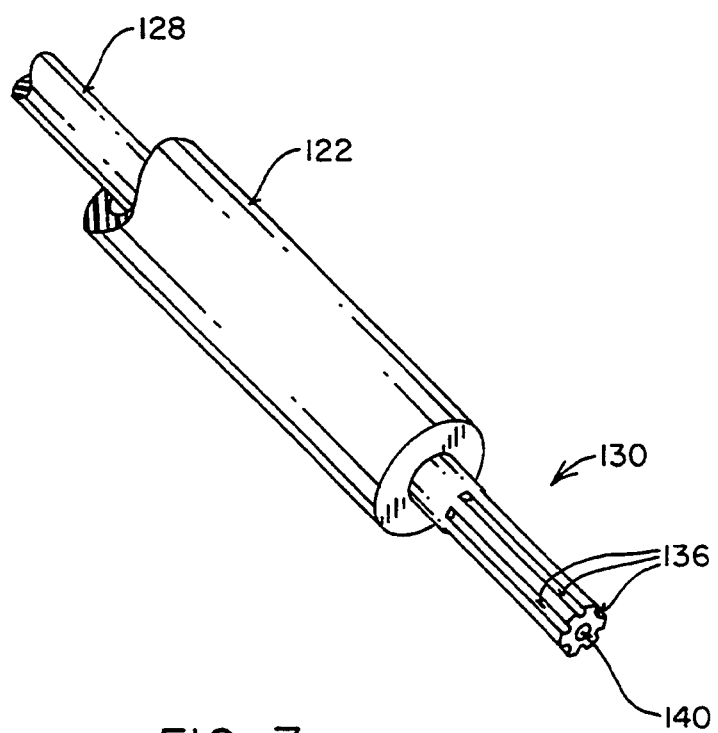
FIG. 7 is a detailed view of the distal end of the dissection device of FIG. 6, illustrating the dissection head.

Referring now to FIGS. 6 and 7, a dissection device 120 constructed in accordance with the principles of the present invention will be described. The dissection device 120 comprises a rigid shaft 122 having a distal end 124 and a proximal end 126. A drive shaft 128 extends through a central lumen of the shaft 122 and terminates in a dissection head 130 at its proximal end. A handle 132 is connected to the proximal end 126 of shaft 122 and includes a motor drive means capable of rotating or oscillating the drive shaft 128. The frequency of rotation (or oscillation) will typically be from about 2000 rpm (or Hz) to 20,000 rpm (or Hz), preferably being in the range from about 5000 rpm (or Hz) to 10,000 rpm (or Hz). A switch 144 will be provided on handle 132 for turning on and off the dissection head 130.

The dissection head 130 is formed as a cylindrical body having a plurality of axial channels 136 formed therein. The cylindrical body has a length generally in the range from about 2 mm to 20 mm, preferably being in the range from about 5 mm to 15 mm, and a diameter in the range from about 1 mm to 10 mm, preferably in the range from about 1.5 mm to 4 mm. Usually, from about 4 to 10 axial channels will be formed, more usually being equally circumferentially spaced-apart.

The dissection device 120 is particularly well suited for introduction through a trocar sleeve for use in laparoscopic and other minimally invasive surgical procedures. The diameter of shaft 122 will be sufficiently small to permit such introduction, typically being 5 mm or less. The dissection device 120 is used by contacting the dissection head 130 at the dissection boundary, i.e., the interface between the tissue and body structure to be dissected from the tissue, and initiating rotation and/or oscillation of the head. Use of the high frequency rotation or oscillation has been found to provide a relatively clean separation between the tissue and body structure with minimal risk of bleeding, perforation, or other undesirable injuries.

Preferably, the dissection device 20 will further include an electrode 140 at its distal tip. Electrode 140 can be connected to a conventional electrocautery power supply, typically a monopolar power supply through a connector 142 which is disposed at the proximal end of the handle 132. Thus, the dissection device 120 can be used to cauterize any cuts or tears which are accidentally caused, without need to introduce a separate electrocautery device.

Figure 8C:
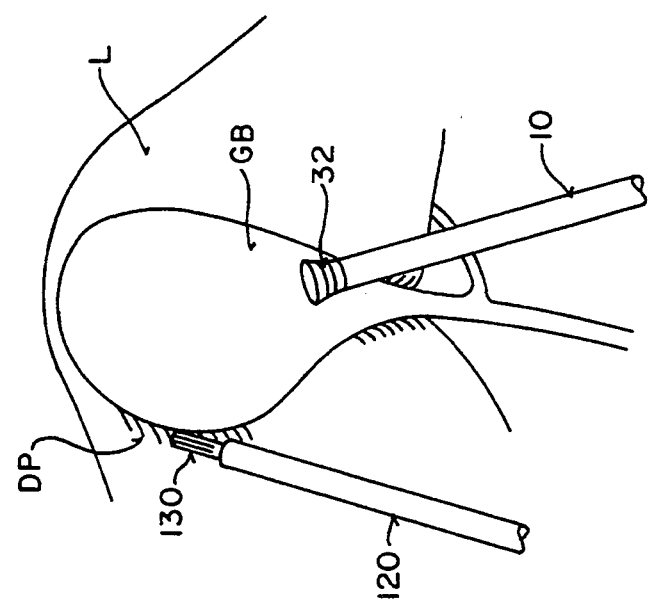
FIGS. 8A–8C illustrate the method of the present invention for manipulating and dissecting a gallbladder.
Figure 8B:
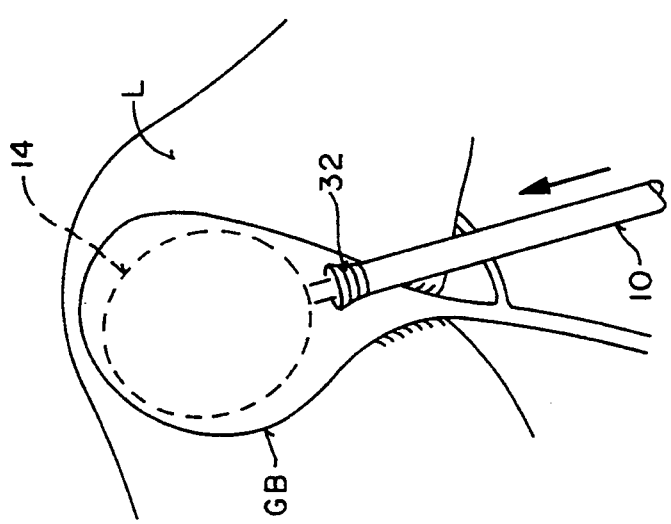
Figure 8A:
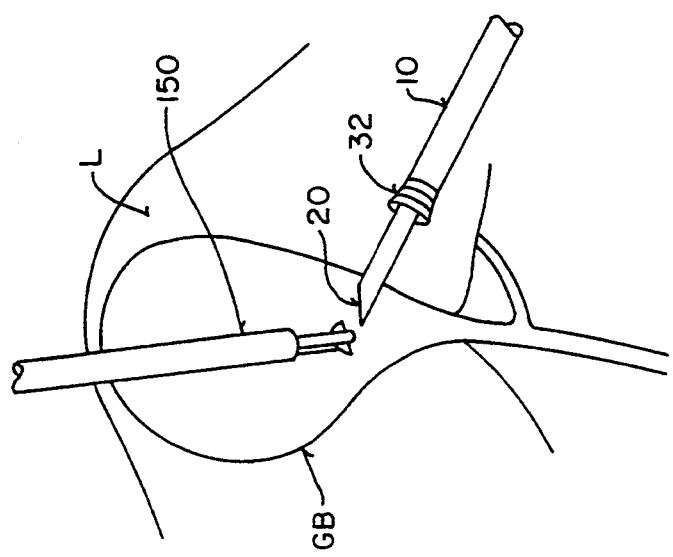

Referring now to FIGS. 8A-8C, use of the manipulation device 10 and the dissection device 120 for performing a gallbladder removal procedure (cholecystectomy) will be described. The figures illustrate the gallbladder GB being dissected from the liver L. The instruments utilized, including both the manipulation device 10 and the dissection device 120, will have been introduced through conventional trocar sheaths in a well known manner for performing laparoscopic cholecystectomy.

Initially, a portion of the outside wall of the gallbladder GB is grasped with a conventional forceps grasper 150, as illustrated in FIG. 8A. The sharp tip 20 of the manipulator device 10 is then penetrated through the wall of the gallbladder GB next to the region which is held in place by the graspers 150.

After the penetration has been achieved, device 10 is advanced forward until the resilient tip 32 forms a seal about the site of penetration, as illustrated in FIG. 8B. The sharp tip 20 will be retracted by axially translating the tube 22 in a proximal direction, and the contents of the gallbladder (bile) will be withdrawn through the interior lumen of the shaft 12. After the contents have been largely drained, the balloon 14 is inflated (as illustrated in broken line in FIG. 8B) to fill the void which has been left and expand the gallbladder GB, usually distending the gallbladder slightly to improve control and access. The device 10 may then be used to manipulate the gallbladder GB and expose the dissection plane DP, i.e. the interstitial plane between the gallbladder and the liver bed L.

The tissue dissection device 120 is next introduced, and the dissection head 130 contacted with the dissection plane DP (FIG. 8C). The dissection head 130 is actuated and used to carefully separate the exposed wall of the gallbladder GB from the liver bed L. It will be appreciated that the manipulator device 10 will be constantly repositioned to expose the dissection plane DP in an optimum manner. The dissection is continued until the gallbladder GB is completely detached from the liver bed L and other surrounding tissue. The inflated balloon 14 can then be deflated, the manipulator device 10 withdrawn, and the gallbladder removed through a trocar sleeve in a conventional manner.

Although the foregoing invention has been described in detail for purposes of clarity of understanding, it will be obvious that certain modifications may be practiced within the scope of the appended claims.

What is claimed is:

1. A method for dissecting a hollow body structure, said method comprising:
   introducing an expandable member on the distal end of a rigid shaft into an interior volume of the hollow body structure;
   expanding the expandable member to occupy at least a major portion of the interior volume sufficient to allow manipulation of substantially all of the hollow body structure; and
   separating attachment of the hollow body structure from surrounding tissues while simultaneously manipulating the rigid shaft to reposition the hollow body structure.

2. A method as in claim 1, wherein the expandable member is introduced through a previously formed penetration through a wall of the hollow body structure.

3. A method as in claim 2, wherein the penetration was formed by advancing a sharp tip at the distal end of the shaft through the wall.

4. A method as in claim 3, further comprising protecting the sharp tip after it has entered the interior of the hollow body structure.

5. A method as in claim 1, wherein the expandable member is introduced through a natural body orifice.

6. A method as in claim 1, further comprising aspirating fluid from the interior of the hollow body structure to prevent loss to the surrounding tissue.

7. A method as in claim 6, wherein the aspirating step includes aspiration from both the interior of the hollow body structure and from the site around the penetration through the wall.

8. A method as in claim 1, wherein the expandable member is an elastic balloon which is expanded by introducing an inflation medium.

9. A method as in claim 1, wherein the separating step includes exposing a dissection plane between the structure and surrounding tissue to a rotating or oscillating dissection head, wherein said head has axial channels spaced about its periphery.

10. A method for dissecting a gallbladder from surrounding tissue, said method comprising:
    forming a penetration through a wall of the gallbladder;
    aspirating bile from the interior of the gallbladder;
    introducing an expandable member on the distal end of a rigid shaft into the interior of the gallbladder;
    expanding the expandable member to occupy substantially the entire interior volume of the gallbladder to allow for the manipulation of substantially all of the gallbladder; and
    separating attachment of the gallbladder from surrounding tissues while simultaneously manipulating the rigid shaft to reposition the gallbladder in order to expose the dissection plane.

11. A method as in claim 10, wherein the penetration is formed by advancing a sharp tip disposed at the end of the shaft through the wall of the gallbladder, wherein said sharp tip is on a tube mounted coaxially about the rigid shaft.

12. A method as in claim 11, further comprising retracting the tube to protect the sharp tip after the expandable balloon has been introduced.

13. A method as in claim 10, wherein the penetration is formed by advancing a sharp tip which is formed integrally at the distal end of the rigid shaft.

14. A method as in claim 13, further comprising extending a rod having a blunt tip proximally of the sharp tip to protect the sharp tip after the expandable balloon has been introduced.

15. A method as in claim 10, wherein the bile is aspirated through at least one lumen concentric with the rigid shaft.

16. A method as in claim 15, wherein the bile is aspirated through a first lumen interior to the rigid shaft and a second concentric lumen exterior to the rigid shaft, wherein said first lumen aspirates bile from the interior of the gallbladder and the second lumen aspirates bile from the site of shaft penetration.

17. A method as in claim 16, wherein bile is aspirated simultaneously through both the first and second lumens.

18. A method as in claim 10, wherein the expandable member is an elastic balloon which is expanded by introducing an inflation medium.

19. A method for dissecting a gallbladder from surrounding tissue, said method comprising:
    forming a penetration through a wall of the gallbladder;
    aspirating bile from the interior of the gallbladder;
    introducing an expandable member on the distal end of a rigid shaft into the interior of the gallbladder;
    expanding the expandable member until the gallbladder is distended; and
    separating attachment of the gallbladder from surrounding tissues while simultaneously manipulating the rigid shaft to reposition the gallbladder in order to expose the dissection plane.

20. A method as in claim 19, wherein the gallbladder is separated by contacting a dissection plane between the gallbladder and surrounding tissue with a rotating or oscillating dissection head, wherein said head has axial grooves spaced apart about its periphery.

21. A device for manipulating a hollow body structure, said device comprising:

a rigid shaft having a proximal end and a distal end;

an expandable member disposed near the distal end of the shaft;

means for selectively expanding the expandable member from an unexpanded configuration to an expanded configuration;

a sharp tip and a blunt tip disposed near the distal end of the rigid shaft;

means for axially translating the sharp tip relative to the blunt tip, whereby either tip can be selectively exposed at the distal end of the rigid shaft;

means near the distal tip of the rigid shaft for aspirating fluid to near the proximal end of the shaft, wherein the aspirating means includes an axial lumen extending from the distal end to the proximal end of the rigid shaft and a separate tube coaxially mounted with an axial lumen extending from the distal end to the proximal end of the rigid shaft; and a sleeve mounted coaxially over the rigid shaft and means for aspirating the interior of the sleeve, wherein the sleeve has a resilient tip which can conform to the exterior of the body structure, wherein the resilient tip extends over at least a portion of the expandable member, so that the tip will be compressed when the expandable member is inserted into a body structure.

22. A device as in claim 21, wherein the means for axially translating comprises a tube mounted coaxially with the rigid shaft, wherein the tube has a sharp tip and the shaft has a blunt tip.

23. A device as in claim 22, wherein the tube is mounted coaxially over the outside of the shaft.

24. A device as in claim 21, wherein the means for axially translating comprises a tube mounted coaxially with the rigid shaft, wherein the tube has a blunt tip and the shaft has a sharp tip.

25. A device as in claim 24, wherein the rigid shaft has an axial lumen and the tube is mounted coaxially within said axial lumen.

26. A device as in claim 21, wherein the expandable member is an elastic balloon and the means for selectively expanding comprises an inflation lumen extending from the proximal end of the rigid shaft to the balloon.

27. A device as in claim 26, wherein the inflation lumen is disposed coaxially about the rigid shaft.

28. A device for manipulating a hollow body structure, said device comprising:

a rigid shaft having a proximal end and a distal end;

means disposed near the distal end of the rigid shaft for piercing a wall of the hollow body structure;

an expandable member disposed near the distal end of the rigid shaft;

means for selectively expanding the expandable member from an unexpanded configuration to an expanded configuration; and means for aspirating fluid from near the distal end of the shaft to the proximal end, wherein the means for aspirating comprises an aspiration lumen within the rigid shaft, wherein the means for aspirating further comprises a sleeve mounted coaxially over the rigid shaft, wherein the sleeve has a resilient tip which can conform to the exterior of the body structure, wherein the resilient tip extends over at least a portion of the expandable member, so that the tip will be compressed when the expandable member is inserted into a body structure.

29. A device as in claim 28, wherein the piercing means comprises a sharp tip on the rigid shaft.

30. A device as in claim 28, wherein the piercing means comprises a coaxial tube having a sharp tip.

31. A device as in claim 28, wherein the expandable member is an elastic balloon and the means for selectively expanding comprises an inflation lumen extending from the proximal end of the rigid shaft to the balloon.

* * * * *